(12) United States Patent
Fritzen et al.

(10) Patent No.: US 9,212,194 B2
(45) Date of Patent: Dec. 15, 2015

(54) FUNCTIONALIZED PARTICLES AND USE THEREOF

(75) Inventors: Petra Fritzen, Moers (DE); Bernd Rohe, Moers (DE)

(73) Assignee: SACHTLEBEN CHEMIE GMBH, Duisburg (DE)

( * ) Notice: Subject to any disclaimer, the term of this patent is extended or adjusted under 35 U.S.C. 154(b) by 250 days.

(21) Appl. No.: 13/698,289

(22) PCT Filed: May 19, 2011

(86) PCT No.: PCT/DE2011/075116
§ 371 (c)(1),
(2), (4) Date: Dec. 14, 2012

(87) PCT Pub. No.: WO2012/025105
PCT Pub. Date: Mar. 1, 2012

(65) Prior Publication Data
US 2013/0096235 A1    Apr. 18, 2013

(30) Foreign Application Priority Data
May 20, 2010 (DE) .......................... 10 2010 029 190

(51) Int. Cl.
| | |
|---|---|
| *C07F 7/18* | (2006.01) |
| *B82Y 30/00* | (2011.01) |
| *C09C 1/02* | (2006.01) |
| *C09C 1/06* | (2006.01) |
| *C09C 1/36* | (2006.01) |
| *C09C 3/12* | (2006.01) |
| *C09D 5/03* | (2006.01) |
| *C09D 7/12* | (2006.01) |
| *C07F 7/28* | (2006.01) |
| *C08K 9/06* | (2006.01) |
| *B82Y 40/00* | (2011.01) |

(52) U.S. Cl.
CPC ............... *C07F 7/1868* (2013.01); *B82Y 30/00* (2013.01); *C07F 7/1892* (2013.01); *C07F 7/28* (2013.01); *C09C 1/027* (2013.01); *C09C 1/06* (2013.01); *C09C 1/3684* (2013.01); *C09C 1/3692* (2013.01); *C09C 3/12* (2013.01); *C09D 5/033* (2013.01); *C09D 7/1225* (2013.01); *B82Y 40/00* (2013.01); *C01P 2004/51* (2013.01); *C01P 2004/61* (2013.01); *C01P 2004/62* (2013.01); *C01P 2004/64* (2013.01); *C01P 2004/84* (2013.01); *C01P 2006/60* (2013.01); *C01P 2006/62* (2013.01); *C08K 9/06* (2013.01); *Y10S 977/773* (2013.01); *Y10S 977/788* (2013.01); *Y10S 977/896* (2013.01); *Y10T 428/2982* (2015.01)

(58) Field of Classification Search
CPC ............ C08K 3/10; C08L 83/08; C08L 83/10
USPC ............. 524/265; 523/456, 205; 428/402
See application file for complete search history.

(56) References Cited

U.S. PATENT DOCUMENTS

| | | | |
|---|---|---|---|
| 6,207,783 B1 * | 3/2001 | Petty et al. ..................... | 528/33 |
| 6,325,846 B1 | 12/2001 | Bagala et al. | |
| 8,119,730 B2 * | 2/2012 | Edelmann et al. ............ | 524/588 |
| 2003/0018103 A1 | 1/2003 | Bardman et al. | |
| 2009/0318594 A1 * | 12/2009 | Grothe et al. ................. | 524/148 |

FOREIGN PATENT DOCUMENTS

| | | |
|---|---|---|
| EP | 0755986 A2 | 1/1997 |
| EP | 2050796 A1 | 4/2009 |
| WO | 2005/003218 A1 | 1/2005 |
| WO | 2007/084245 A1 | 7/2007 |
| WO | 2008/023073 A1 | 2/2008 |

OTHER PUBLICATIONS

"CoatOSil 142 Silane." Optima Tech News. East Water Magazine. pp. 2-16, Jul. 2011.*
English abstract of WO 2008/023073.
International Search Report and Written Opinion dated Jan. 24, 2012.
International app. No. PCT/DE2011/075116, English Translation of International Preliminary Report on Patentability, dated Nov. 2012.
English abstract of EP2050796 (A1).

* cited by examiner

*Primary Examiner* — Hannah Pak
(74) *Attorney, Agent, or Firm* — Cahn & Samuels, LLP

(57) ABSTRACT

A method of making a powder coating composition includes obtaining functionalized particles by reacting inorganic particles with alkoxysilanes having the general structural formula (I) $R^1Si(OR^2)_3$, silane oligomers having the general structural formula (II) $(R^1)(OR^2)_2Si-O-[-Si(R^1)(OR^2)-O-]_m-Si(R^1)(OR^2)_2$ or mixtures thereof.

13 Claims, 4 Drawing Sheets

FUNCTIONALIZED PARTICLES AND USE THEREOF

This U.S. patent application is a national stage application of PCT/DE2011/075116 filed on 19 May 2011 and claims priority of German patent document 10 2010 029 190.0 filed on 20 May 2010, the entirety of which is incorporated herein by reference.

The present invention relates to functionalized particles, to methods for producing such functionalized particles, and to the use of the functionalized particles for producing coating materials and the use thereof to coat articles, especially in combination of the functionalized particles with compounds containing reactive groups, including monomers, and also to the articles thus coated. The application of this combination of the functionalized particles with reactive monomers in thin layers on substrates such as metal, wood, and plastics results in improved scratch resistance, abrasion resistance, stone chip resistance, corrosion protection, adhesion, chemical resistance, color stability, and/or thermal stability on the part of the substrates thus coated.

BACKGROUND OF INVENTION

Long gone are the days when coatings fulfilled merely a decorative purpose—instead, they serve to protect the underlying substrates and incorporate diverse additional functions. It is therefore desirable to unite as many properties as possible in one coating.

The coating materials encompass, fundamentally, size colors, lime paints, varnishes, stains and glazes, emulsion paints, polymer-resin paints, and powder coatings. The coating materials used to produce coatings have already been much described in the prior art. Often employed in the coating materials are chemical compounds with reactive groups and composite particles, which crosslink on curing and produce coatings adhering to the substrate.

For instance, EP 2050796 B1 describes a coating with enhanced hiding power, compositions produced therefrom, and methods for production thereof, that are produced using composite particles. The method described in EP 2050796 B1 produces composite particles comprising a pigment particle and a plurality of polymer particles, with each of the polymer particles comprising at least one reacted complementary functional group which forms a covalent bond with the pigment particle. For this purpose, inorganic pigments are suspended in alcohols, and are functionalized by addition of long-chain monofunctional alkoxysilanes, and then polymer particles are added to the suspension, and are intended to produce a spacer effect and thereby to counteract the flocculation of the pigment particles. The functionalized particles are used in the form of a suspension, as a dispersion coating with a solvent content.

As well as solvent-containing systems there are also coating materials which are used in the form of "dry" mixtures. Powder coatings of this kind are likewise well known in the prior art. Generally speaking, these powder coatings comprise binders, additives, colorants, and fillers, but no solvents. The chemical differences between the raw materials used in powder coatings and in conventional coating materials are not great, and the crosslinking mechanisms of a powder coating film resemble those of a baking varnish, where two reactants form an organic network under the influence of temperature and thereby enter into a chemical union. Virtually all raw materials for powder coatings are present generally in the form of powder.

For reasons including primarily those of economics, fillers are used in powder coatings. The most frequently used fillers include calcium carbonate, heavy spar, and precipitated barium sulfate. A disadvantage of powder coating systems comprising filler is that they possess a poor hot water resistance. This can be attributed to the poor attachment of the binder to the filler surface. Water is able to penetrate into the microcracks that are present, and this may lead to altered optical properties, such as bleaching, for example, and even to poor corrosion resistance.

The pigments that are known in the prior art and are used in powder coatings are in some cases equipped with an organic aftertreatment, based for example on a polyalcohol, this aftertreatment being bonded only physically, via dipole-dipole bonds or van der Waals bonds, to the pigment surface. The primary contribution of these interactions is to improve wetting when the pigments are incorporated, but they do not contribute to steric stabilization. Such stabilization can be achieved, however, via the addition of suitable additives.

A disadvantage of the stabilizing components used hitherto, though, is that they tend to migrate. This leads to a deterioration in the optical properties (gloss, hue) and also in the service properties (e.g., corrosion resistance, hot water resistance).

SUMMARY OF INVENTION

The inventors have found that functionalized particles, especially titanium dioxide particles and barium sulfate particles, having reactive functional groups bonded covalently to the particles, lead not only to an improved hiding power but also, in particular, to an improved hot water resistance, particularly in powder coating systems. As a result it is possible to produce thinner layers on application, while retaining the hiding power, and these layers undergo significantly less color alteration under the influence of hot water. Hence the user of the powder coating is provided with both a technical advantage and an economic advantage, and obtains a coating having improved properties such as scratch resistance, abrasion resistance, stone chip resistance, corrosion resistance, adhesion, chemical resistance, hiding power, color stability, and thermal stability, more particularly hot water resistance.

The invention is therefore directed to functionalized particles which comprise inorganic particles with straight-chain or branched-chain hydrocarbon radicals that are bonded chemically to them via —O—Si— units, said radicals having 1 to 20, preferably 1 to 10 carbon atoms, with at least one reactive group on the hydrocarbon radical that is able to form a further chemical bond with a reactant. In accordance with the invention, a straight-chain or branched-chain hydrocarbon radical of this kind is bonded to the particle surface via at least one —O—Si— unit. The formation of an Si—O—Si backbone structure is advantageous, where a plurality of such Si—O units which carry at least one hydrocarbon radical bind to the particle surface in order to reinforce the attachment of the hydrocarbon radicals having 1 to 20, preferably 1 to 10, carbon atoms with at least one reactive group on the hydrocarbon radical to the particle surface.

As chemically reactive compounds for producing the functionalized particles that are capable of reacting with the particle surface and also with further materials containing reactive groups, such as epoxy resins, by forming covalent bonds, the invention uses, as well as alkoxysilanes having the general structural formula (I) $R^1Si(OR^2)_3$, especially silanol oligomers having the general structural formula (II)

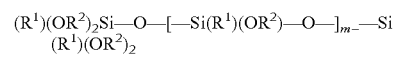

or mixtures thereof. In the formulae given above, $R^1$ is a nonhydrolyzable, aliphatic, straight-chain or branched-chain hydrocarbon radical having 1 to 18, preferably having 1 to 10, carbon atoms, also with —O— in the chain, having at least one, preferably terminal, chemically reactive group which is able to enter into an addition reaction or condensation reaction, preferably selected from amino, epoxy, vinyl, and methacrylate, $R^2$ is H or a hydrolyzable group, preferably —OR with $R=C_1-C_{18}$ alkyl, especially $C_1-C_{10}$ alkyl, and m is 0-10; and in the formulae given above, the groups $R^1$ and $R^2$ may each also be different radicals. Although the radicals $R^2$ may all be present in the form of $C_1-C_{18}$ alkyl as defined above within one molecule of the structural formula (I) or (II), it is also possible in general for partially hydrolyzed compounds to be used that have one or more OH groups, which on further hydrolysis give up a smaller amount of $C_1-C_{18}$ alcohol.

The silanol oligomers which can be used in accordance with the invention have an —Si—O—Si— backbone structure, with there being attached to each Si atom in the chain a nonhydrolyzable, aliphatic, straight-chain or branched-chain hydrocarbon radical having 1 to 18, preferably having 1 to 10, carbon atoms, which may also have at least one ether unit —C—O—C— in the chain and which—preferably terminally—has at least one functional (chemically reactive) group, selected from amino, epoxy, vinyl, and methacrylate, which is able to enter into addition reactions or condensation reactions with functional groups of other compounds such as monomers and also one (terminally two) group(s) —$OR^2$, where $R^2$ is hydrogen or a hydrolyzable group, preferably —OR with $R=C_1-C_{18}$ alkyl. Accordingly, each Si atom in the chain has one or two adjacent Si atoms bonded via —O—, and, in contrast to the silanes which exhibit exclusively T0 signals in 29Si NMR, the silane oligomers used in the invention thus possess exclusively Si atoms which are characterized as T1 and T2 atoms by means of 29Si NMR. On the basis of this backbone molecular structure, the coupling of just one OH group on the particle surface has a fixing effect, which thus forces the coupling of the entire silane oligomer via the further —$OR^2$ groups. Examples of silane oligomers which can be used are, in accordance with the invention, CoatOSil 142 Silane® (prehydrolyzed aminosilane from Momentive) or CoatOSil MP200 Silane® (prehydrolyzed epoxy silane from Momentive), which can be used to functionalize the particles.

Particles which can be used for the functionalized particles (functionalized pigments and functionalized fillers in the sense of this invention are inorganic particles such as barium sulfate, inorganically aftertreated barium sulfate, zinc sulfide, inorganically aftertreated zinc sulfide, lithopones, inorganically aftertreated lithopones, calcium carbonate, inorganically aftertreated calcium carbonate, and titanium dioxide with the inorganic aftertreatments known to the skilled person, with a chemically reactive molecule which is capable of reacting with reactive oxygen atoms (e.g., in hydroxyl groups) of the particle surface, and so a covalent bond is formed.

Consequently, as well as the functionalized particles, which may be functionalized pigments or functionalized fillers, the invention also relates to the method for producing the functionalized inorganic particles, by reacting inorganic particles with alkoxysilanes having the general structural formula (I) $R^1Si(OR^2)_3$, silane oligomers having the general structural formula (II)

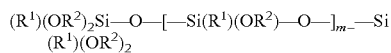

or mixtures thereof. In the case of production in a liquid phase, the resulting suspension, which is generally an aqueous suspension, can be subjected to drying and the reaction product can be subjected optionally to grinding, and in the formulae (I) and (II) above:

$R^1$ is a nonhydrolyzable, aliphatic, straight-chain or branched-chain hydrocarbon radical having 1 to 18, preferably a group having 1 to 10, carbon atoms, also with —O— in the chain, having at least one, preferably terminal, chemically reactive group which is able to enter into an addition reaction or condensation reaction, preferably selected from amino, epoxy, vinyl, and methacrylate, $R^2$ is H or a hydrolyzable group, preferably —OR with $R=C_1-C_{18}$ alkyl, especially $C_1-C_{10}$ alkyl, and m is 0-10.

In the formulae above, the groups $R^1$ and $R^2$ may each also stand for different radicals in one molecule.

The functionalized particles thus produced can be incorporated by known methods into coating materials, and the chemically reactive groups, selected from amino, epoxy, vinyl, and methacrylate, on the hydrocarbon radicals may enter into addition reactions or condensation reactions with reactive groups in the coating material and may thus produce coating properties which are improved in terms of the properties.

The method described by the inventors for producing the functionalized particles is relatively advantageous environmentally and economically. The method of the invention does entirely without alcohol as solvents, and without other solvents, and is therefore more eco-friendly, since no hazardous substances, no substances injurious to health, and no other organic components are released. Moreover, there are no specific workplace safety-relevant aspects to be borne in mind when producing and handling the reactants and products (such as apparatus with explosion protection measures, for example).

In comparison to the prior art, the synthesis of the functionalized particles in accordance with the invention is notable for fewer operating steps. The product is in powder form and is therefore storage-stable and is notable for its flexibility in incorporation into all common reactive monomer systems which are able to form thin layers. The product is therefore in the form of a 100% active ingredient. There can be no systemic incompatibilities (such as flocculation or formation of gel particles) with other reactants of the monomer/binder system. There is therefore no need at all to add polymer particles which are used as spacers.

DETAILED DESCRIPTION OF INVENTION

Figure 1:
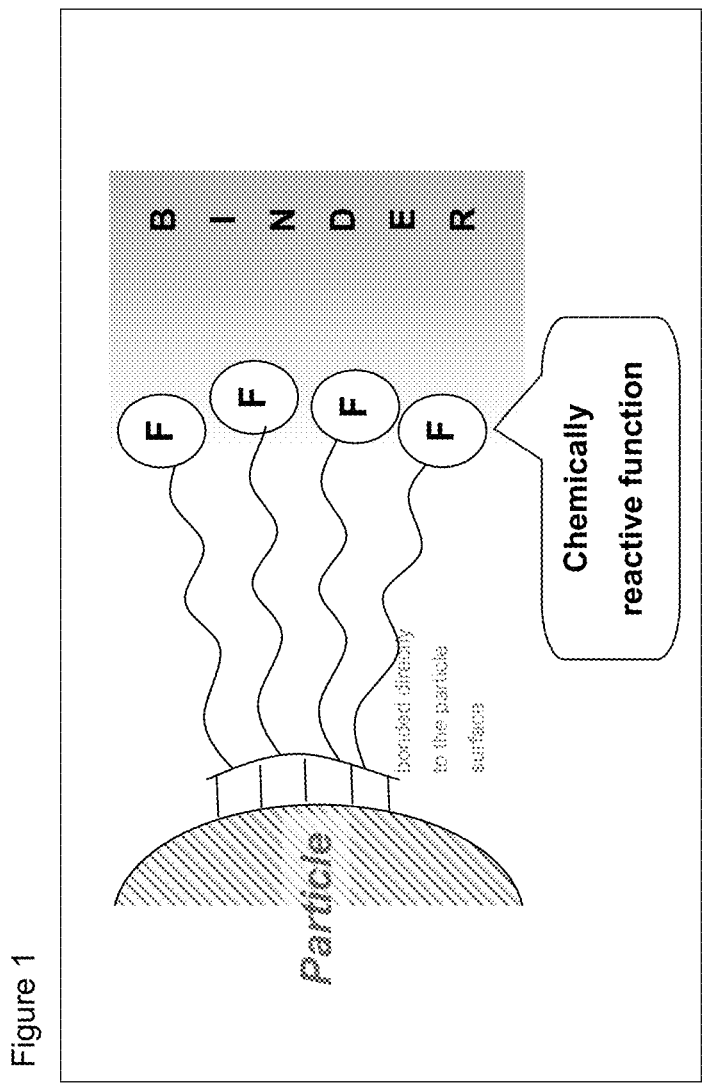
FIG. 1 shows a schematic representation of the use of functionalized particles in reactive monomer/binder systems for the purpose of forming thin layers having a layer thickness of up to 200 μm, more particularly 50 to 100 μm.

In accordance with the invention, a combination of functionalized particles and compounds with reactive monomers as binder or constituents thereof, which are able to form such thin layers, has the effect, on the basis of its chemical structure, of improvements in respect of properties such as scratch resistance, abrasion resistance, stone chip resistance, corrosion protection, adhesion, chemical resistance, color stability, thermal stability, and hot water resistance. The inventors have found that by adding functionalized particles to binder systems that are able to form thin layers, such properties are combined with one another.

By means of the compounds with reactive groups, which may also be monomers, oligomers or prepolymers each having corresponding functional groups that are able to interact with the reactive groups of functionalized particles, it is possible to prepare the following polymeric binder matrices: acrylate (co)polymers, vinyl acetate polymers, vinyl/acrylate polymers, styrene/acrylate copolymers, polyurethanes, polyureas, polyepoxides, polyvinyl chloride, ethylene/vinyl acetate polymers, styrene/butadiene polymers, polyesters, polyamides, polyethers, and mixtures thereof. The functionalized particles can be incorporated into the compounds having the reactive groups, and then the mixture is used to coat surfaces.

The invention is elucidated hereinbelow on the example of coating systems such as powder coating compositions, without being confined thereto. The invention is thus also directed to powder coating compositions comprising such functionalized particles, more particularly functionalized titanium dioxide particles and functionalized $BaSO_4$ particles, the radicals with functional groups being bonded covalently via the —SiO— units to the surface of the particle.

The invention is therefore also directed to a powder coating composition which comprises
a. 20% to 80% by weight of binder,
b. 5% to 60% by weight of inorganic pigment or mineral filler,
c. 5% to 60% by weight of functionalized inorganic particles,
d. 0.1% to 10% by weight of additive, selected from flow, leveling, and deaerating additives or mixtures thereof,
with all of the ingredients together making 100% by weight.

In one embodiment of the powder coating composition of the invention, the functionalized inorganic particles, which may be pigment or filler are present in an amount of 10% to 50% by weight, particularly 30% to 40% by weight.

In a further embodiment of the powder coating composition of the invention, the inorganic pigment or the mineral filler is present in an amount of 10% to 50% by weight, particularly 30% to 40% by weight.

The powder coating composition of the invention may further comprise up to 15% by weight of colorants, selected from color pigment and dye, or mixtures thereof.

To improve the bonding between functionalized pigment and binder it is possible for the powder coating composition of the invention to comprise up to 10% by weight of crosslinking assistants, selected from crosslinkers, catalysts or mixtures thereof.

The particle functionalized with reactive radicals is generally selected from titanium dioxide particles or barium sulfate particles. The barium sulfate here may have been subjected to an inorganic pretreatment in order to cause the subsequently applied compounds having the structural formulae (I) and (II) to interact more effectively with the barium sulfate particles.

By virtue of the functional groups, the reactive radicals adhere directly by covalent bonds to the particle surface, thereby preventing migration of the particles in the coating. Moreover, such reactive end groups on the reactive functional radicals allow incorporation into the polymer system, thereby anchoring the particle in the polymer and improving stabilization against flocculation. Another advantage is that there is no need for an additional additive for stabilization during powder coating production. This further simplifies the complexity of the formula.

The principal components of the coating system of the invention, such as of a powder coating system, are the binder, which may also be a mixture of two or more binder components, and the functionalized particles. Combinations of pigment and filler are state of the art or a basis of this invention, provided the mixture at least comprises functionalized particles (filler or pigment).

|  | Inorganic pigment | Inorganic pigment (functionalized) | No inorganic pigment (organic pigment instead) |
| --- | --- | --- | --- |
| Filler | State of the art | Inventive composition | State of the art |
| Filler (functionalized) | Inventive composition | Inventive composition | Inventive composition |
| No filler | State of the art | Inventive composition | State of the art |

The binder, as the basis, forms the coating film, which envelops all of the particulate solids in the coating material. The selection of the binder substantially determines the physical properties of the powder coating and hence its sphere of use. The binders thus determine the fundamental properties such as surface quality, hardness, and stability of the coating film, and they consist in general of long-chain organic compounds which contain reactive groups which are able to react with one another and also with the functionalized particles, if necessary via a curing agent/crosslinker, to form branched macromolecules. For the inventive compositions for powder coatings it is therefore preferred to employ synthetic resins which can crosslink with one another.

As binders it is therefore possible in accordance with the invention, in principle, to use epoxy resins, carboxyl- and hydroxyl-containing polyesters, acrylate resins, and also polyurethane resins, or hybrid systems of the aforementioned resins. Suitable with preference are systems containing epoxy groups.

As mentioned, the binder may further comprise curing agents/crosslinkers. Substances which can be used as curing agents, depending on the binder system, are triglycidyl isocyanurate (TGIC) and hydroxylalkylamide for polyester resins, and also dodecanedioic acid. The use of hydroxylalkylamide is preferred.

Generally it is possible for the following curing agents to be employed:
Phenolic curing agents, imidazoline derivatives, anhydride adducts, modified dicyandiamide, epoxy resin, hydroxyalkylamide curing agents, aromatic glycidyl esters, isocyanate adduct, and blocked uretdiones.

As leveling/flow agents it is possible to use castor oil derivatives and polyacrylate resins.

As a deaerating additive it is possible to use benzoin.

As fillers it is possible to use the following synthetic and natural minerals: heavy spar, feldspar, chalk, finely ground quartz/quartz sand, synthetic barium sulfate, aluminum trihydroxide, wollastonite, zinc sulfide, lithopones, calcium carbonate (GCC and NCC), silica (coated and uncoated), nepheline syenite, mica, talc, and kaolin.

The functionalized particles, more particularly titanium dioxide particles or barium sulfate particles, with covalently bonded, reactive functional radicals, are mixed, as a component essential to the invention, with the binder.

Particles of this kind provided with reactive functional organic radicals, especially titanium dioxide and barium sulfate particles, can be produced by the method as already elucidated above.

On the one hand, this may involve functionalization in an aqueous phase. On the other hand, the organic component with organic radicals featuring the reactive groups thereon may be applied to the particle surface, for functionalization, by direct spraying and subsequent mixing/grinding.

Where the surface of the particles does not have any reactive groups such as (—O—)/=O groups or hydroxyl groups which are able to interact with the reactive groups of the organic radicals, as in the case of $BaSO_4$, for example, such pigments/fillers may be subjected to an inorganic pretreatment, by which such groups are provided by means, for example, of precipitation of metal oxides on the surface of the $BaSO_4$ particles, or joint precipitation therewith.

Such inorganic surface modification of a barium sulfate consists typically of at least one inorganic compound, selected from aluminum, antimony, barium, calcium, cerium, chlorine, cobalt, iron, phosphorus, carbon, manganese, oxygen, sulfur, silicon, nitrogen, strontium, vanadium, zinc, tin, and/or zirconium compounds and/or salts. Examples include sodium silicate, sodium aluminate, and aluminum sulfate.

The inorganic surface treatment of $BaSO_4$ may take place in aqueous suspension. In that case the reaction temperature is preferably not to exceed 50° C. The pH of the suspension is set to pH values in the range greater than 9, using NaOH, for example. With vigorous stirring, the aftertreatment chemicals (inorganic compounds), preferably water-soluble inorganic compounds such as, for example, aluminum, antimony, barium, calcium, cerium, chlorine, cobalt, iron, phosphorus, carbon, manganese, oxygen, sulfur, silicon, nitrogen, strontium, vanadium, zinc, tin, and/or zirconium compounds or salts, are added. The pH and the amounts of aftertreatment chemicals are selected in accordance with the invention such that the latter are present completely in solution in water. The suspension is stirred intensively so that the aftertreatment chemicals are homogeneously dispersed in the suspension, and preferably for at least 5 minutes. In the next step, the pH of the suspension is lowered. It has proven advantageous here to lower the pH slowly and with vigorous stirring. With particular advantage the pH is lowered within from 10 to 90 minutes to levels of 5 to 8. This is then followed in accordance with the invention by an aging time, preferably an aging time of around an hour. The temperatures during this time ought preferably not to exceed 50° C. The aqueous suspension is then washed and dried. Appropriate for the drying of functionalized $BaSO_4$ is, for example, spray drying, freeze drying and/or drying by grinding. Depending on the drying method, a subsequent grinding of the dried powders may be necessary. The grinding may be carried out by methods that are known per se.

For the functionalization, the compounds of the formula (I) and (II) that have been described above as being suitable in accordance with the invention can be added, with vigorous stirring and/or during a dispersing operation, to a suspension of the particles, such as to a titanium dioxide suspension or to a suspension of inorganically pretreated barium sulfate. The reactive functional organic radicals become bonded to the particle surface.

In accordance with the invention, the functionalized particles such as titanium dioxide particles and also the inorganically aftertreated fillers such as barium sulfate particles, via the functional radicals, have one or more functional groups, examples being one or more hydroxyl, amino, carboxyl, epoxy, vinyl, methacrylate and/or isocyanate groups, thiols, alkyl thiocarboxylates, disulfidic and/or polysulfidic groups. Thus the functionalized particles are bonded via a functional group(s) to the particles and are able via another functional group(s) to interact with the polymeric matrix. The reactive end group(s) of the functionalizing component allow(s) incorporation into the polymer system, thereby anchoring the pigment particle in the polymer.

For the functionalization of inorganic particles or inorganically pretreated particles, as for example for the production of silanized, functionalized $BaSO_4$ particles, it is possible for an aqueous $BaSO_4$ suspension of $BaSO_4$ particles that have already been organically surface-modified to be further modified with at least one silane. Silanes which can be used are, as described above, alkoxyalkylsilanes of the formula (I), the alkoxyalkylsilanes being selected more preferably from octyltriethoxysilane, gamma-methacrylo-propyltrimethoxysilane, gamma-glycidyloxypropyltri-methoxysilane, gamma-aminopropyltriethoxysilane, gamma-aminopropyltrimethoxysilane, gamma-isocyanatopropyltri-ethoxysilane, and vinyltrimethoxysilane. Used with particular preference for functionalizing the particles are silane oligomers of the structural formula (II) such as CoatOSil 142 Silane® (prehydrolyzed amino silane from Momentive) or CoatOSil MP200 Silane® (prehydrolyzed epoxy silane from Momentive). For this purpose it is possible, before or after washing, for a $BaSO_4$ suspension of inorganically surface-modified $BaSO_4$ particles to be admixed, with vigorous stirring or with dispersing, with the siloxane compound such as an alkoxyalkylsilane or silane oligomer. This is followed in accordance with the invention by an aging time, preferably an aging time of 10 to 60 minutes, preferably at temperatures of not more than 40° C. The subsequent procedure may then be as already described. Alternatively a silane oligomer of the formula (I) or II) may also be applied, after drying, to the inorganically modified particles, by mixing.

Suitable compounds having reactive functional radicals, in addition to the silane oligomers, silanes, siloxanes, and polysiloxanes, are organic phosphoric and phosphoric acids, and also titanates and zirconates.

The functionalized particles, such as a titanium dioxide pigment, for example, are preferably dried before being mixed with other ingredients of the coating material. This drying may be carried out by methods that are known per se. Particularly appropriate for drying is the use of convection dryers, spray dryers, grinding dryers, freeze dryers and/or pulsation dryers. Other dryers, however, can also be used in accordance with the invention. Depending on the drying method, subsequent grinding of the dry powders may be necessary. This grinding may be carried out by methods that are known per se.

The particles modified organically with the functional radicals preferably have an average particle diameter of d50=1 nm to 100 µm, preferably of d50=1 nm to 3 µm, more preferably of d50=5 nm to 1 µm, and prior to organic modification are preferably in a form in which they are dispersed to primary particle size.

In accordance with the invention, the particles used in the powder coating of the invention, based for example on titanium dioxide, are able to provide a maximum, very high, hiding power and lightening power in a coating system, being present with optimum dispersion, as primary particles, in the surrounding medium. This may be supported by an optimized dispersing technology, in which case the following points should be borne in mind:

1. wetting
2. mechanical disruption
3. stabilization against flocculation

After wetting and the mechanical disruption of the agglomerates, a key factor in powder coatings, especially in the melt and also during extrusion, and during the baking process, is the stabilization of the individual particles. This can be realized in particular by means of the steric stabilization of the invention.

After wetting and the mechanical disruption of the agglomerates, a key factor in powder coatings, especially in the melt and also during extrusion, and during the baking process, is the stabilization of the individual particles. This can be realized in particular by means of the steric stabilization of the invention.

The powder coating composition of the invention can therefore be used advantageously to coat articles. In this way it is therefore possible to provide powder coatings which are suitable for a multiplicity of applications, such as for the coating of metals such as metal pipes, for example, household appliances such as washing machines, oven surrounds, fume exhaust hoods, for example, sanitary articles such as washstand and bathroom fittings, bath tubs, shower trays, and shower surround profiles, for example, interior automobile fittings, and automobile bodies. The invention is therefore also directed to the articles coated with the powder coatings of the invention.

The invention is elucidated further by the following preparation and use examples.

PREPARATION EXAMPLES

The functionalized particles which can be used in accordance with the invention for powder coatings in the compositions of the invention, possessing covalently bonded, reactive functional radicals, are prepared as follows in the preparation examples below.

Preparation Example 1

In this preparation example a $TiO_2$ rutile pigment was subjected to an organic aftertreatment as follows.

20 kg of Hombitan R210 (rutile pigment) filtercake with a solids content of 50% are dispersed in 20 liters of water, using a dissolver at 750 rpm, for 30 minutes. Added to this suspension are 1.5% (based on solids) of CoatOSil MP200 Silane® (prehydrolyzed epoxysilane from Momentive), and mixing is continued for five minutes at a speed of 750 rpm. The suspension is subsequently dried via a spraying tower with an entry temperature of 400° C. and an exit temperature of 120° C. The discharge from the spray dryer may optimally also be ground using a pinned disk mill or jet mill.

Preparation Example 2

In this preparation example a $BaSO_4$ pigment was subjected to an organic aftertreatment as follows.

$BaSO_4$ filtercake with 35% solids content and a $d_{50.3}$ of the volume distribution of $d_{50.3}=0.7$ μm (measured using a CPS disk centrifuge, model DC2400 from CPS, USA)
deionized water with a conductivity of approximately 3 μS/cm
5% strength aqueous sodium hydroxide solution
5% strength hydrochloric acid
$Na_2SiO_3$ solution with 384 g $SiO_2$/l
$NaAlO_2$ solution with 262 g $Al_2O_3$/l
BaS solution with 50-55 g BaS/l 2500 g of $BaSO_4$ paste were weighed out into a glass beaker and suspended with deionized $H_2O$ to give 3300 g. The suspension was heated to 70° C. and then adjusted to a pH of 7 using aqueous sodium hydroxide solution. A barium excess of around 5 g $Ba^{2+}$/l was then set using 350 ml of BaS solution. The pH was again adjusted to 7, using hydrochloric acid, and then $Na_2SiO_3$ solution (0.1% $SiO_2$ based on $BaSO_4$) was added. The pH was adjusted to 4 using hydrochloric acid, and the suspension was aged for 30 minutes. Aqueous sodium hydroxide solution was used to set a pH of 6.0, which was maintained during addition of $NaAlO_2$ solution (0.2% $Al_2O_3$ based on $BaSO_4$). This was followed by adjustment to a pH of 7.0 and aging for 30 minutes. Thereafter the suspension was filtered through a suction filter and washed to a conductivity of <300 μS/cm. The filtercake is redispersed in deionized water and, based on the solids content, 1.5% of CoatOSil 142 Silane® (prehydrolyzed aminosilane from Momentive) was added to the suspension. After an aging time of 15 minutes, the suspension is spray-dried.

USE EXAMPLES

Investigation of the Hiding Power

In accordance with the formulas indicated in Table 1, powder coating compositions were produced and were investigated for their hiding power.

TABLE 1

| Component | 1 | 2 | 3 | 4 | 5 |
|---|---|---|---|---|---|
| Binder: polyester | 1755.0 | 1755.0 | 1755.0 | 1755.0 | 1755.0 |
| Binder: epoxy | 1170.0 | 1170.0 | 1170.0 | 1170.0 | 1170.0 |
| Leveling agent | 25.0 | 25.0 | 25.0 | 25.0 | 25.0 |
| Degassing agent | 50.0 | 50.0 | 50.0 | 50.0 | 50.0 |
| Sachtleben R210 | 2000.0 | | | | |
| TiO2 rutile without organic AT | | 2000.0 | | | |
| TiO2 rutile with 1% by weight reactive functionalization A | | | 2000.0 | | |
| TiO2 rutile with 2% by weight reactive functionalization A | | | | 2000.0 | |
| TiO2 rutile with 1% by weight reactive functionalization B | | | | | 2000.0 |

AT: aftertreatment

Processing of the Formulas

The formula components were premixed in a mixer at 1000 rpm for 1 hour. The extrusions were carried out at a screw speed of 300 rpm, a barrel temperature of 100° C. and a feed quantity of 45 kg/h. The powders were applied using a corona gun at 60 KV.

Determination of the Hiding Power

Figure 2:
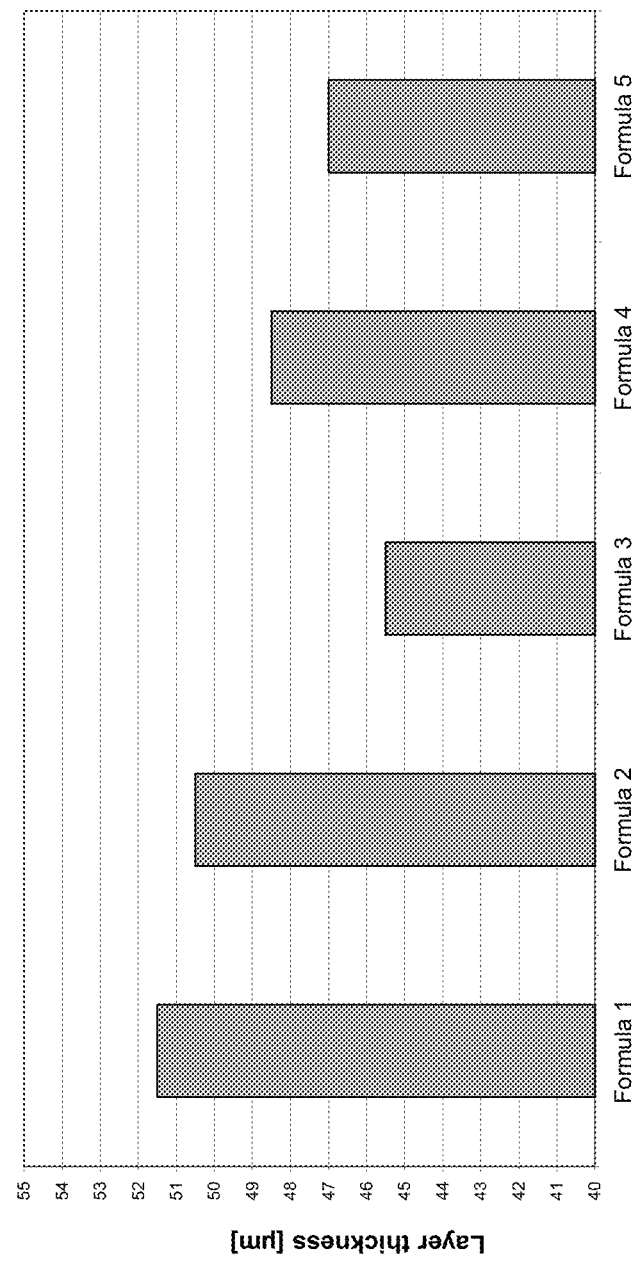
FIG. 2 shows the determination of hiding power of powder coatings.

For the determination of the hiding power, the powder coating was applied to a phosphated steel panel attached to which was an aluminum contrast foil with chessboard pattern. The powder coating was applied to the substrate uniformly, with a layer thickness decreasing from top to bottom, and then baked at 180° C. for 20 minutes. Baking was followed by a visual determination of the point at which the background of the aluminum contrast foil was no longer visible. The associated layer thickness was determined using a layer thickness measuring device. The result of the determination of the hiding power is shown in FIG. 2. Inventive formulas (3-5) allow a reduction in layer thicknesses by up to 15% as compared with the prior-art formulas (1:2), signifying a considerable saving in terms of powder coating used.

Investigation of the Hot Water Resistance

In accordance with the formulas indicated in Table 2, powder coating compositions were produced and were investigated for their hot water resistance.

TABLE 2

| Component | 1 | 2 | 3 | 4 | 5 | 6 |
|---|---|---|---|---|---|---|
| Binder: polyester | 4196 | 2517.5 | 2517.5 | 2517.5 | 2517.5 | 2517.5 |
| Curing agent | 221 | 132.5 | 132.5 | 132.5 | 132.5 | 132.5 |
| Leveling agent | 83.5 | 50 | 50 | 50 | 50 | 50 |
| Degassing agent | 41.5 | 25 | 25 | 25 | 25 | 25 |
| Heliogen Blue K6907 | | 5 | 5 | 5 | 5 | 5 |
| Titanium dioxide (rutile) | 416.5 | 250 | 250 | 250 | 250 | 250 |
| Barium sulfate 1 (synth., 3 μm, no AT) | 2000 | | | | | |
| Barium sulfate 2 (synth., 0.7 μm, organic AT: amine) | | 2000 | | | | |
| Barium sulfate 3 (synth., 0.7 μm, inorganic AT, organic AT: amine) | | | 2000 | | | |
| Barium sulfate 4 (synth., 0.7 μm, with reactive functionalization) | | | | 2000 | | |
| Barium sulfate 5 (heavy spar, 1 μm) | | | | | 2000 | |
| Calcium carbonate (GCC) | | | | | | 1227.5 |

AT: aftertreatment

Processing of the Formulas

The formula components were premixed in a mixer at 1000 rpm for 1 hour. The extrusions were carried out at a screw speed of 300 rpm, a barrel temperature of 100° C. and a feed quantity of 45 kg/h. The powders were applied using a corona gun at 60 KV at a layer thickness of 60 μm. The powder coatings were cured at 180° C. for 20 minutes.

Determination of the Hot Water Resistance

Figure 3:
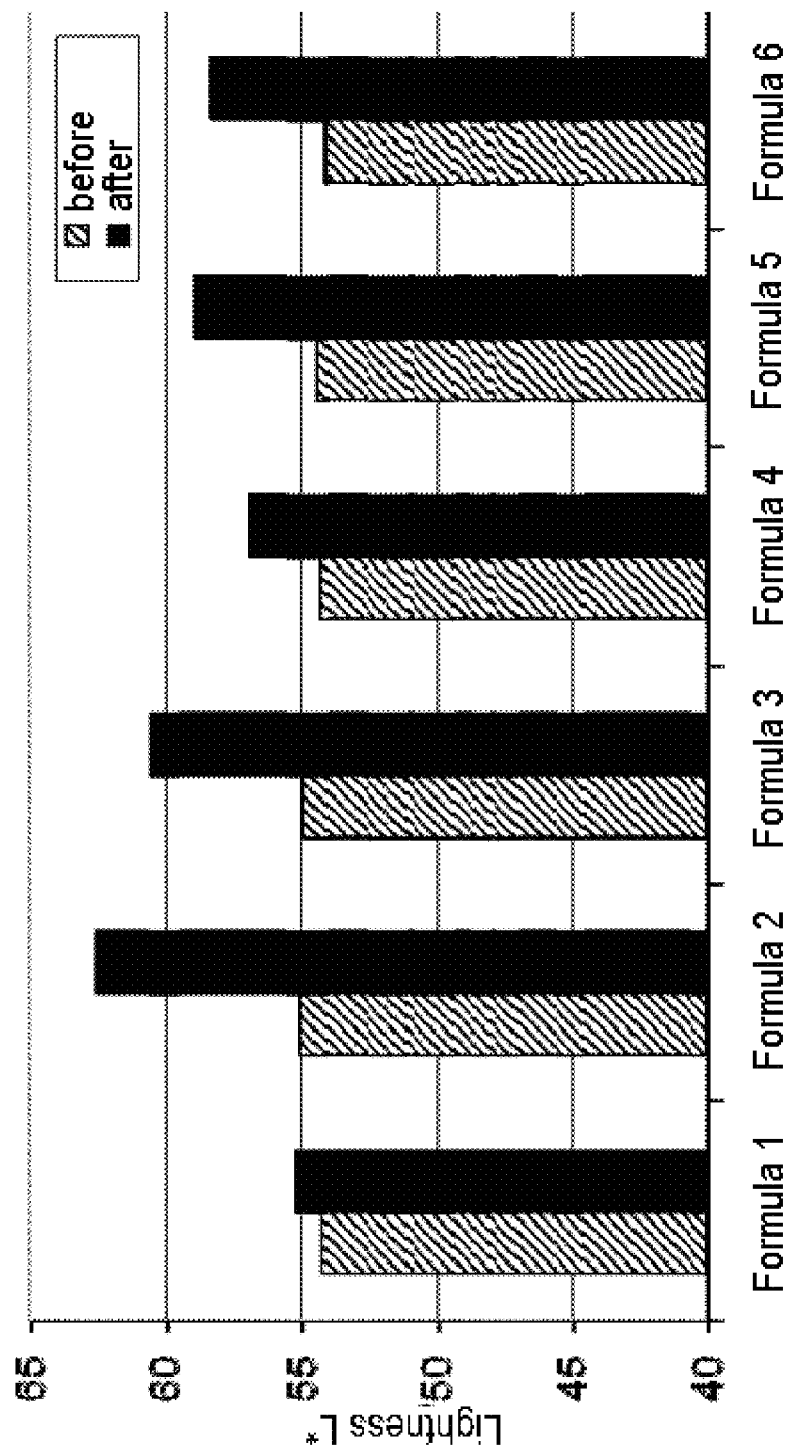
FIG. 3 shows measurements for color difference data of powder coatings.
Figure 4:
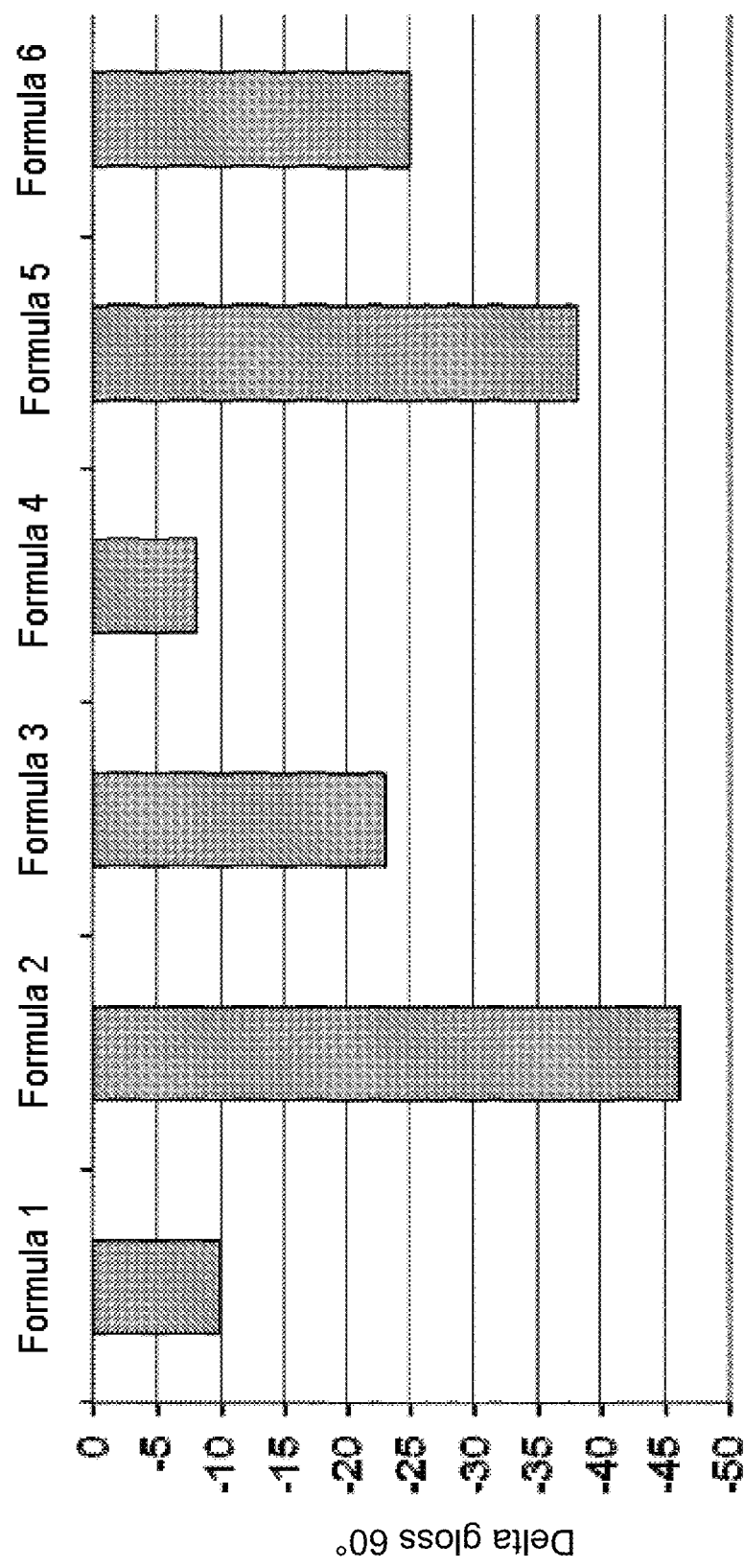
FIG. 4 shows measurements for gloss data of powder coatings.

The powder coating was half-immersed in water at 70° C. for 8 hours and then measured for its color difference data (FIG. 3) and gloss (FIG. 4).

As shown in FIG. 3 for the effect of different fillers on the lightness L* and in FIG. 4 for the effect of different fillers on the change in the 60° gloss, in each case before and after hot water exposure at 70° C. for 8 hours, inventive formula 4 has a positive effect on the lightness and on the change in gloss of the coatings.

TABLE 3

| | Lightness L* Before | After | Delta L* | 60° gloss Before | After | Delta gloss 60° |
|---|---|---|---|---|---|---|
| Formula 1 | 54.3 | 55.2 | 1.0 | 90 | 80 | −10 |
| Formula 2 | 55.0 | 62.7 | 7.6 | 73 | 27 | −46 |
| Formula 3 | 54.9 | 60.6 | 5.7 | 82 | 59 | −23 |
| Formula 4 | 54.3 | 57.0 | 2.7 | 71 | 63 | −8 |
| Formula 5 | 54.4 | 59.0 | 4.6 | 79 | 41 | −38 |
| Formula 6 | 54.1 | 58.5 | 4.3 | 71 | 46 | −25 |

The invention claimed is:

1. A method of producing functionalized particles by reacting inorganic particles with a silane oligomer having the general structural formula (II)

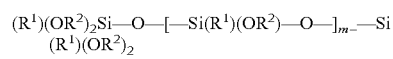

or mixtures thereof, and

If necessary, subjecting a resulting reaction mixture to drying, wherein:

$R^1$ is a nonhydrolyzable, aliphatic, straight-chain or branched-chain hydrocarbon radical having 1 to 18 carbon atoms, with —O— in the chain, having at least one functional group which is able to enter in an addition reaction or condensation reaction, and wherein said at least one functional group of $R^1$ is selected from the group consisting of amino, epoxy, vinyl, and methacrylate, $R^2$ is H or a hydrolysable group, and m=0-10.

2. The method as claimed in claim 1, wherein $R^2$ is $C_1$-$C_{18}$ alkyl.

3. The method as claimed in claim 1, wherein the inorganic particles comprise titanium dioxide particles or barium sulfate particles.

4. The method as claimed in claim 3, wherein the inorganic particles comprise barium sulfate particles, and the method further comprises subjecting barium sulfate to an inorganic pretreatment.

5. Functionalized inorganic particles obtained by the method of claim 1.

6. Inorganic particles functionalized with silane oligomers having the general structural formula (II)

$$(R^1)(OR^2)_2Si-O-[-Si(R^1)(OR^2)-O-]_m-Si(R^1)(OR^2)_2$$

wherein:

$R^1$ is a nonhydrolyzable, aliphatic, straight-chain or branched-chain hydrocarbon radical having 1 to 18 carbon atoms, with —O— in the chain, having at least one functional group which is able to enter in an addition reaction or condensation reaction, and wherein said at least one functional group of $R^1$ is selected from the group consisting of amino, epoxy, vinyl, and methacrylate, $R^2$ is H or a hydrolysable group, and m=0-10.

7. The inorganic particles according to claim 6, wherein $R^2$ is $C_1$-$C_{18}$ alkyl.

8. The inorganic particles according to claim 6, wherein the inorganic particles comprise titanium dioxide particles or barium sulfate particles.

9. A coating composition, comprising:
the inorganic functionalized particles according to claim 6; and compounds having functional groups which react with the functional groups of the particles to form chemical bonds.

10. The coating composition according to claim 9, wherein the composition is in form of a powder coating composition.

11. The coating composition as claimed in claim 9, comprising:

20% to 80% by weight of binder,

5% to 60% by weight of inorganic pigment or mineral filler,

5% to 60% by weight of functionalized inorganic particles, 0.1 to 10.0% by weight of additives selected from the group consisting of flow, leveling, and deaerating additives or mixtures thereof, which all of the ingredients together making 100% by weight.

12. The coating composition as claimed in claim 11, wherein the functionalized inorganic particles are present in an amount of 10% to 50% by weight.

13. An article coated with the coating composition as claimed in claim 9.

* * * * *